United States Patent [19]

Sengewald

[11] Patent Number: 4,709,534

[45] Date of Patent: Dec. 1, 1987

[54] BAG FOR INFUSION SOLUTIONS AND THE LIKE AND METHOD OF MANUFACTURING THE SAME

[76] Inventor: Karl-Heinz Sengewald, Postfach 1460, 4801 Halle in Westf. 1, Fed. Rep. of Germany

[21] Appl. No.: 770,001

[22] Filed: Aug. 26, 1985

Related U.S. Application Data

[63] Continuation of Ser. No. 471,140, Mar. 1, 1983, abandoned.

[30] Foreign Application Priority Data

May 15, 1982 [DE] Fed. Rep. of Germany ....... 3218415

[51] Int. Cl.$^4$ .................................................. B65B 3/02
[52] U.S. Cl. ........................................ 53/452; 53/450; 53/449; 156/244.13
[58] Field of Search ..................... 53/51, 425, 411, 450, 53/451, 452, 555, 455, 462, 170, 449; 193/193, 195, 196, 198, 210, 238, 933; 206/390; 383/41; 604/408; 156/198, 244.13, 290, 244.19, 244.14

[56] References Cited

U.S. PATENT DOCUMENTS

| 2,271,714 | 2/1942 | Ray ...................................... 493/196 |
| 3,210,908 | 10/1965 | Samberg ........................... 53/555 X |
| 3,245,197 | 4/1966 | Van Mil, Jr. et al. ............. 53/555 X |
| 3,319,538 | 5/1967 | Bodolay et al. ................... 53/455 X |
| 3,372,797 | 3/1968 | Grevich ............................. 53/455 X |
| 3,453,797 | 7/1969 | Soto .................................... 53/452 X |
| 3,540,183 | 11/1970 | Bodolay et al. ................... 53/455 X |
| 3,545,983 | 12/1970 | Woods ............................... 53/451 X |
| 3,651,615 | 3/1972 | Bohner et al. ........................ 53/452 |
| 3,759,379 | 9/1973 | Wrede ................................. 604/408 |
| 3,832,827 | 9/1974 | Lemelson ............................. 53/425 |
| 4,010,786 | 3/1977 | Aquettant et al. ..................... 383/41 |
| 4,063,641 | 12/1977 | Kuehn et al. ........................ 206/484 |
| 4,124,965 | 11/1978 | Stahl ................................... 53/452 X |
| 4,231,832 | 11/1980 | Weikert ....................... 156/244.19 X |
| 4,332,122 | 6/1982 | Williams ............................. 604/408 |
| 4,450,028 | 5/1984 | Vilutis ......................... 156/244.13 X |
| 4,474,634 | 10/1984 | Hiraoka et al. ............. 156/244.14 X |

FOREIGN PATENT DOCUMENTS

| 267184 | 12/1964 | Australia .............................. 206/390 |
| 2010359 | 9/1971 | Fed. Rep. of Germany ......... 53/455 |
| 38126 | 3/1980 | Japan ................................... 604/408 |

Primary Examiner—Robert L. Spruill
Assistant Examiner—Steven P. Weihrouch
Attorney, Agent, or Firm—Michael J. Striker

[57] ABSTRACT

A bag for infusion solutions and the like has a body part formed by a hose and having walls composed of a synthetic thermoplastic compound foil, and at least one connecting part formed of one piece with the body part and also composed of the foil. A hose for manufacturing the bags is formed so that the bags extend transverse to the direction of elongation of the hose and their connecting parts face toward one longitudinal edge of the hose. The bags are manufactured by producing first a hose element of a synthetic thermoplastic foil in aseptic conditions, and then placing onto the hose elements at both sides a layer of another synthetic thermoplastic foil by lamination, so as to form the hose, whereupon the bags are produced on the thus formed hose.

15 Claims, 11 Drawing Figures

U.S. Patent  Dec. 1, 1987  Sheet 1 of 3  4,709,534
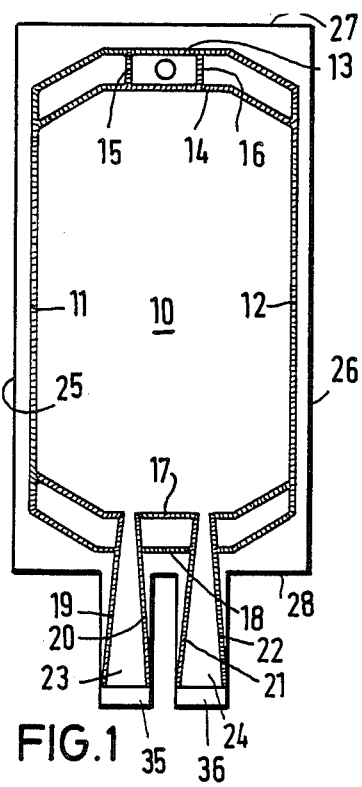
FIG.1
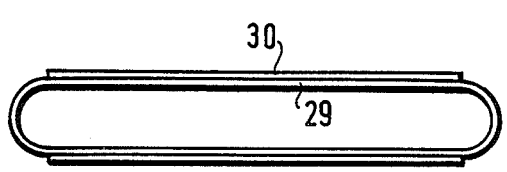
FIG.2
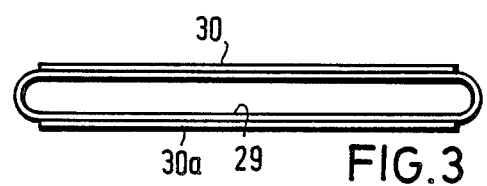
FIG.3
FIG.4
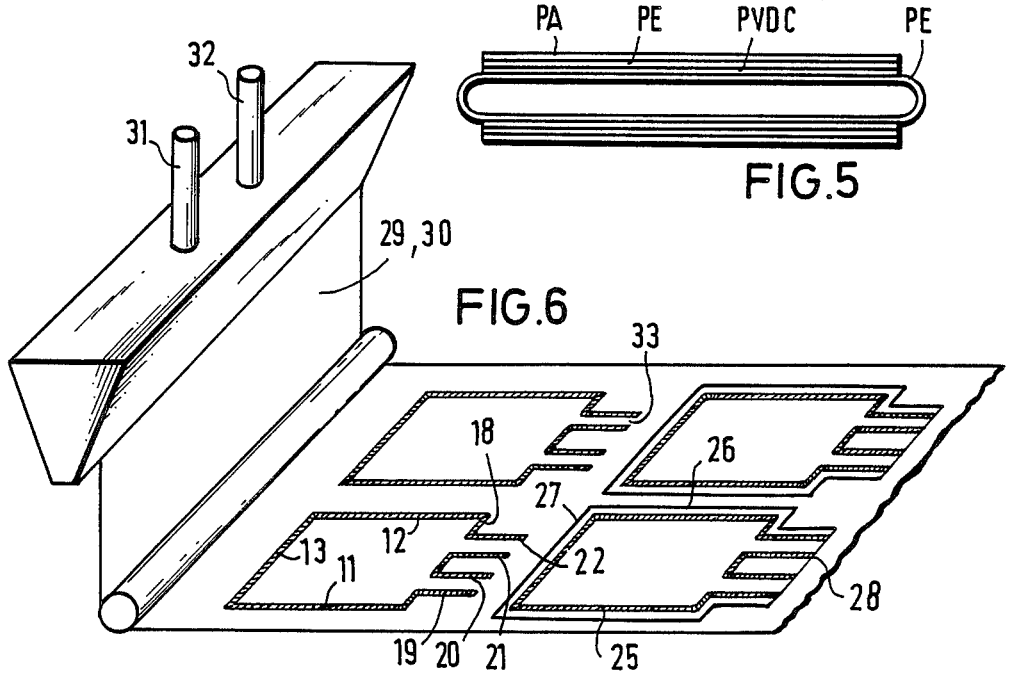
FIG.5
FIG.6

BAG FOR INFUSION SOLUTIONS AND THE LIKE AND METHOD OF MANUFACTURING THE SAME

This application is a continuation of application Ser. No. 471,140, filed Mar. 1, 1983 now abandoned.

BACKGROUND OF THE INVENTION

The present invention relates to a bag for infusion solutions, and the like, and to a method of manufacturing and filling the same, for example for CAPD solutions for a continuous ambulant peritonic dialysis, and also infusion solutions. These substances must be supplied from sterile conditions.

In many cases, containers of glass or synthetic plastic material are utilized. Since these containers are produced by blowing processes, it is possible only with great difficulty to provide air for blowing the containers without bacteria. The bottles must be thoroughly cleaned and sterilized before their filling.

It was proposed to use bags for infusion solutions composed of synthetic thermoplastic foils such as soft polyvinyl chloride. A hose is used for manufacturing of these bags, and with the flat-lying hose its width corresponds to the width of the bags to be produced, so that no welding of foil layers at the longitudinal edges extending in direction of elongation of the hose takes place. Since the bags have different widths or the filled bags must have different dimensions, it is necessary to start the manufacture with a hose of the respective width, so that for manufacturing these infusion bags with different widths and diameters a respective number of blowing molds must be provided. The bottom region of the bag is provided with two transverse welding seams spaced from one another, and punched openings for suspending the bags during their utilization are provided between these transverse seams.

In the known infusion bags composed of soft polyvinyl chloride, special connecting parts are provided for filling and also for damping of the bags. The connecting parts are formed so that special pipes of synthetic plastic material connected with the hose material are arranged between both foil layers of the hose. The special arrangement of the pipes makes the manufacture of the infusion bags more expensive.

As long as the front ends of these pipes are not closed, this takes place first, and then the bag is filled with the infusion solution. This has the disadvantage that damaging particles can deposit on the freely accessible inner walls of the pipes, for example from air. This air can also reach a certain region between both foil layers of the bag, since at the front ends of the open pipes extending into the bag, when their walls do not abut against one another, also both foil layers which form the hose of the bag are not in abutment. As a result of this, the bag of soft polyvinyl chloride with inserted pipes cannot be held free from bacteria many times and prior to its filling must be sterilized in the region of the pipes. Since also the manufacture of the original hose must be performed in aseptic conditions, the known bags, also those composed of soft polyvinyl chloride, provided with the filling or emptying pipes must be further sterilized prior to their filling. Moreover, infusion bags of soft polyvinyl chloride can be welded very easily; however, they do not have high strength.

SUMMARY OF THE INVENTION

Accordingly, it is an object of the present invention to provide a bag for infusion solutions and the like, and a method of manufacturing the same, which avoids the disadvantages of the prior art.

More particularly, it is an object of the present invention to provide a bag for infusion solutions and the like, which can be produced and filled in a simple manner and in aseptic conditions sterile and suitable with high strength for various infusion solutions.

In keeping with these objects and with others which will become apparent hereinafter, one feature of the present invention resides, briefly stated, in a bag for infusion solutions and the like, which has a body part formed by a hose and having walls composed of a synthetic thermoplastic compound foil, and one or several connecting parts which are formed of one piece with the body part and also composed of this foil.

Since the bag is composed of a compound foil, it has a high strength and stability, inasmuch as it is possible to select the foil layers connected with one another by welding with consideration of their strength and easy connection by welding, as well as the stability.

Since the connecting part or parts are of one piece with the body of the bag and also composed of the above mentioned compound foil, there is the advantage that not only the foil layers of the bag tightly abut against one another, but also the foil layers of the connecting parts tightly abut against one another, so that no bacteria or the like damaging elements can enter the connecting parts and the bag.

In accordance with another advantageous feature of the present invention, the inner layer is composed of a polyethylene, and in a further embodiment of polyethylene with increased density equal to advantageously 0.935–0.960 g per cm$^3$ and a thickness of 75 $\mu$m. It can also be composed of polypropylene.

The outer layer is formed as a foil layer of advantageously polyamide. The manufacture of the bag for infusion solutions from a compound foil makes it possible to select as an inner layer a foil which in addition to high weldability also has a composition which is neutral to various infusion solutions. For this purpose especially low pressure polyethylene is suitable.

The outer layer is selected with consideration of the tightness against gas and water vapor and also the protection from the action of radiation, especially solar radiation, onto the infusion solution. At the same time, it must be easily printable. A foil which is suitable for this because of a plurality of advantages is a non-stretchable polyamide foil (Polyamide 6).

In accordance with a further feature of the present invention, each wall of the bag is composed of more than two foil layers, so that for example in direction from outside toward inside foil layers of polyamide, polyethylene, polyvinylidene chloride and polyethylene are provided. In this wall composed of four foil layers the second layer of polyethylene in direction from outside towards inside can be dispensed with.

It is especially advantageous when the wall is composed of three layers including polyamide, oriented polyester with X-coating, and polyethylene.

Polyvinylidene chloride has a very high tightness against the action of oxygen, so that special solutions with or from amino acids are protected.

In the inventive bags composed of the compound foil, both layers of the compound foil are connected with one another by welding, and separating cuts are produced outside of the welding seams. Therefore, starting from a hose with hermetically closed interior, first the bag is formed by welding so that its interior is closed, and then, the bag is cut along its contour by the outwardly located separating cut.

In accordance with a further feature of the invention, the outwardly projecting connecting parts are conical and form passages whose cross section narrows in direction from outside toward inside. It is thereby possible to bring in these connected parts further connecting elements in a simple manner and with reliable adherence.

Still a further feature of the present invention is that the bag in its bottom region and its head region is provided with two transverse welding seams spaced from one another.

Since the inventive bag is produced from the originally sterile hose and the bag remains sterile until its filling and during the latter, it is possible to leave the bags after their manufacture in the hose, so that not to immediately further work the hose, but instead to wind it on a roll and fill the bags at another location. In this process the interiors of the bags can not be contaminated during a long storage or transportation.

The hose with the bags arranged in or on the same can thereby form a separate commercial article. It is especially advantageous when this hose is formed so that the bags extend transverse to the longitudinal direction of the hose with the connecting parts facing towards one longitudinal edge. When the hose is designed in accordance with these features, the connecting parts are accessible in a simple manner, for example from the side of the hose for filling the bags and for example for providing plugs and the like.

It is also possible to arrange the connecting parts with their openings in a series one behind the other. Since the bags are spaced from one another by equal distances, insertion of plugs, filling conduits, and the like, can be performed in this arrangement by a machine. This machine full automatic working process of insertion of plugs or filling conduits, in some cases immediately after the filling or closing the sealing openings, is especially advantageous when during the above described process of manufacture of the bags they remain in or on the hose and connected by the hose to a bag chain. This is attained when between the individual bags formed by welding of the foil layers of the hose, perforation cuts are provided and extend through both hose walls. The perforation cuts have such a length with webs remaining therebetween that a sufficient strength takes place to allow the hose, after forming the contours of the bags, to be wound to a roll or to allow transportation of the hose with the bags through the filling arrangement as a bag chain.

It was already pointed out that, as soon as the bag is produced by welding of both foil layers of the hose, the hose can be opened and the connecting parts which have openings which are not closed by a special welding seam.

It is to be emphasized that both foil layers which form the hose or bag are composed of the compound foil and lie on one another with a certain adherent adhesion. For increasing this adhesion, it can be provided during the manufacture of the hose that the inner layers of the hose abutting against one another are composed of a compound foil which is slightly glued. This can be attained, for example, when in a certain time or space distance after blowing of the initial hose, its inner walls are pressed at the time when the foil layers are glued to one another by the available heat. This small gluing cannot only be controlled by the temperature of the foil hose at the time of their bringing against one another, but also by rollers which press both foil layers of the hose against one another with a respective controllable pressure. This small gluing force is so selected that no air can pass through the filling opening.

It is to be understood that the above described features of bringing the inner foil layers in a slight gluing are preferably provided only in the region of the one piece connecting parts. This means that, for example, in a short time after the production of the inner hose, from both sides of the hose two rollers of small length are available which act only in the region of the subsequently brought connecting parts of the bag. The small gluing of the inner foil layers against one another in the region of the connecting parts is possible, since there later a mechanical spreading of both foil layers apart from one another takes place by insertion of a plug or a filling conduit. From this description it is to be understood that in the region of the connecting parts, possibly only at their front ends, a certain strong gluing can be obtained with the use of the extrusion heat, since the foil layers are separated from one another by mechanical forces.

The sterilization of the bag, regardless of whether the inner walls of the connecting parts abut against one another by adhesion or small gluing, can be increased when despite provision of the perforation cuts the hose is not open. This is performed in accordance with the inventive features in that the perforation cut is made by a heated cutter with corrugations, and thereby the cut surfaces of the foil are connected with one another by welding. As a result of this, by providing the cuts outside of the welding seams for forming the bag, the hose is not opened, since the cutting surfaces are closed by the welding of the foil layers.

In accordance with still another feature of the present invention, the front ends of the connecting parts are spaced from the longitudinal edge of the hose by a certain distance. This solution provides for many advantages. First of all, a free end region is available for cooperation with elements used to transport the hose. These elements can be formed as through openings shaped as perforations in photographic film. In the region of the hose between the longitudinal edge and the connecting parts, special elements for transporting the hose can also be provided, so that the transport arrangement acts in this region and can damage the latter. It is possible to engage the hose for its transportation in the filling station or toward packing arrangement by transport elements in the above mentioned region, for example by seals arranged at both sides and having rough outer surface. Also, in this region rotatable belts can be located between the edge of the hose and the connecting elements at both sides of the hose and act with such pressure that this region is damaged in a certain degree. This is however not dangerous, inasmuch as this region is separated later on.

The invention solution to arrange the front ends of the connecting parts at a certain distance from the edge of the hose has a further advantage that a further safety measure to prevent "opening" of the connecting parts during transportation or storage of the hose in the bag chain can be provided. In accordance with a further feature of the present invention, a further safety element is located in this region to protect the inlet of the connecting part and is closed outwardly, as long as the front openings of the connecting parts are not sufficiently closed by adherence of the inner layers of the foil or gluing of the inner layers of the foil. The strip-shaped region between the front end of the connecting parts and the edge of the hose forms a blocking zone, while in this region the walls of the hose abut against one another, especially as long as no through-openings are provided for transportation of the hose. They also can be made as the perforation cut by heated tools, so that the provision of them does not lead to "opening" of the hose.

In accordance with an inventive method of manufacturing of the bag, the hose at its edge opposite to the connecting parts is first cut in a filling station operating in aseptic condition. Thereby the inlet opening or in general openings of the connecting parts are released, so that as long as they adhere to one another by adhesion of slight gluing, they can be opened by plugs, filling pipes, and the like.

By cutting of the longitudinal edge of the hose, simultaneously a longitudinal passage is formed which also serves for guiding and directing of the bag chain on the filling tools or closing tools.

Despite cutting of the longitudinal edge of the hose, the strip-like region between the edge and the connecting parts of the bag serves further for the purpose of transporting the bag chain, in some cases to a packing arrangement, in which the filled bags are separated in the perforation line by tearing the webs between the perforations. It is also possible to provide filling of the bags and simultaneously tearing the webs between the perforating cuts so as to separate the bags from the hose.

The novel features which are considered characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

FIG. 1 is a plan view of a bag for infusion solutions and the like, in accordance with the present invention;

FIG. 2 is a view showing a section of a hose for manufacturing the inventive bags;

FIG. 3 is a view showing a section of another hose for manufacturing the inventive bags;

FIG. 4 is a view showing a section of a hose with a wall composed of three foil layers;

FIG. 5 is a view showing a section of a hose composed of four foil layers;

FIG. 6 is a perspective and substantially schematic view showing blowing of the hose and manufacturing of the bags;

DESCRIPTION OF THE PREFERRED EMBODIMENTS

Figure 7:
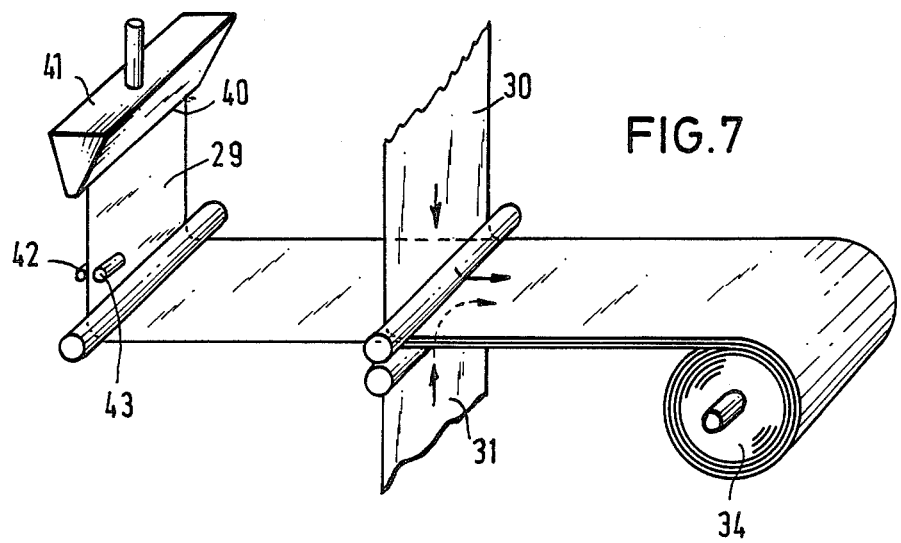
FIG. 7 is a perspective and substantially schematic view of a process of manufacture of a hose.

FIG. 1 shows as an example a bag 10 for liquids which are used in medicine, for example infusion solutions. The bag 10 has welding seams 11 and 12 which extend in a longitudinal direction and connect both foil layers of a hose. The bag 10 also has two transverse welding seams 13 and 14 provided at its bottom end and located at a distance from one another. The transverse welding seams 13 and 14 are connected with one another by a web-like welding seams 15 and 16.

At its head end, the bag 10 has transverse welding seams 17 and 18 which are also arranged at a distance from one another and interrupted by welding seams 19 and 20, as well as 21 and 22. The latter mentioned four seams extend in the longitudinal direction of the bag and form passages for filling or emptying of the bag. The welding seams 19 and 20, as well as 21 and 22 extend so that they converge in direction toward the center of the bag. Thereby, the passages 23 and 24 limited by these seams narrow in direction from outside toward the inside. All above mentioned seams determine the contour or the filling space of the bag 10.

In the region outside of these seams, cuts 25 and 26 are formed at the longitudinal sides of the bag 10. At the bottom end and at the head end cuts 27 and 28 are provided, respectively. The head end of the bag in the region of connecting parts is provided with the above mentioned cuts which extend around the connecting parts designed as the above mentioned passages 23 and 24. The connecting parts are of one piece with the bags, inasmuch as they are composed of the same foil layers.

FIG. 2 shows an original hose for manufacturing the bag in accordance with FIG. 1. It is produced by a coextrusion process so that an inner foil layer 29 is composed of a polyethylene. It is especially advantageous when the inner foil layer 29 is composed of a low-pressure polyethylene with a density of 0.935 g per $cm^3$ and a thickness of $75\mu$. An outer layer 30 is composed of a polyamide with a thickness of $70\mu$.

FIG. 3 shows an inner layer 29 of polyethylene, which is coated with outer foil layers 30 and 30a by lamination. Its manufacture is illustrated in FIG. 7.

FIG. 4 shows a hose of polyethylene PE which is coated by lamination or gluing with a foil of oriented polyester with X-coating OPX or polyvinylidene chloride PVDC, which in turn is coated with a foil of polyamide PA. The hose shown in FIG. 5 has a plurality of foil layers which from outside toward inside include the layers of PA, PE, PVDC and PE.

FIG. 6 shows, as an example, the manufacture of the inventive bag from a composite foil. In an arrangement operating for example in accordance with a coextrusion process for manufacturing a hose, a granulate for the inner layer 29 of polyethylene is supplied via an inlet opening 31, and a granulate for the outer layer 30 of polyamide is supplied via an inlet opening 32. This blowing arrangement is hermetically closed, and blowing of the hose at an extrusion temperature of approximately 170° C. is performed in aseptic conditions.

The hose with both foil layers 29 and 30 is then converted into the bag 10. First, the welding seams 11, 12 as well as 13, 18 and 19, 20 as well as 21, 22 are produced, and thereby both foil layers are connected with one another. Thus, the bag is closed. It is also possible, as shown in FIG. 4, to close the passages 23 and 24 in FIG. 1 by a welding seam 33 provided at their front end. As a rule, this is however not necessary, inasmuch as the foil layers tightly abut against one another. When the above mentioned welding seams 11-22 of the bag are completed, the cuts 25, 26, 27 and 28 shown in FIG. 1 are carried out, and therefore the bag is cut at all its edges. Thereby the hose is opened, but these cuts do not influence the interior of the bag.

As can be seen from FIG. 6, depending upon the width of the hose, two bags located adjacent to one another can be simultaneously manufactured. It is to be understood that the contour cuts 25-28 can also be made in immediate connection with the production of the welding seams 13-22. In other words, the production of the welding seams and the cuts can be carried out by one tool.

The manufacture of the bag is especially advantageous when the original hose of polyethylene PE or polypropylene PP is laminated with further foil layers, inasmuch as, by the selection of these foils in the sense of chemical composition, density and thickness, a special correspondence to specific liquids to be stored in the bag can be provided. FIG. 7, the inlet hose 29 is also blown under aseptic conditions. The foil layers 30 and 31 are laminated onto the latter at both ends. This hose of composite foil is then immediately converted into the bag or wound to a roller 34 which can be further converted, as shown in subsequent Figures, into the bag for infusion solutions.

Figure 8:
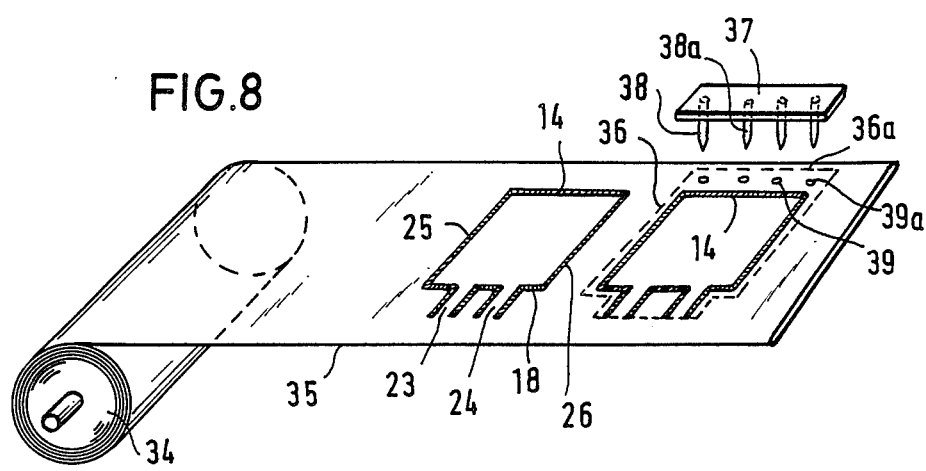
FIG. 8 is a perspective and substantially schematic view showing formation of a plurality of bags in a hose extending transverse to the direction of elongation of the latter.

FIG. 8 shows that the bags produced from the hose wound on the rollers 34 have the connecting parts 23 and 24 which extend transverse to a longitudinal edge 35 of the hose and face toward this edge. The bag shown in FIG. 8 is designed simpler than the bag of FIG. 1. In this bag there are no double welding seams provided in the region of the connecting parts and spaced from one another. Only one welding seam 18 is provided here. Also, in the region of the bottom end only one welding seam 14 which determines the volume of the bag is provided. FIG. 8 further shows that, in addition to the above mentioned welding seams 18, 11, 12 and 14, a perforation 36 is provided. The perforation 36 extends around, in addition to the welding seams, for connecting both foil layers, so that the hose of compound foil material forms a chain of bags, and each bag can be separated from the hose when it is to be filled with the liquid.

For making it possible to hang the bags later on, a perforation line 36a is provided at a greater distance from the bottom welding seam 14. Hanging openings are punched out in the thus retained space. They can be produced advantageously by several heated pins 38, 38a, etc., arranged on a carrier 37. The heated pins are provided so that, simultaneously with making openings, the edges of the cuts are welded with one another. Thereby no "opening" of the hose takes place. Openings 39, 39a, etc., formed by the pins 38 are advantageously arranged at such distances from one another which are equal and extend over the entire length of the hose. Thereby it is possible to use these openings also for other purposes, for example for transporting the hoses with the bags, for example toward or in a filling station for filling of the bag, as will be described hereinbelow.

In accordance with FIG. 8, the front end of the connecting parts 23 and 24 are located at a distance from the hose edge 35, which provides for advantages which will be explained hereinbelow in connection with FIGS. 9 and 10.

For bringing the foil layers of the connecting parts 23 and 24 which later form filling or emptying passages, into such adherence or abutment against one another that no contamination of these passages can take place, rollers 42 and 43 are provided at the end of the extrusion from a nozzle 40 of an extruder 41. The rollers 42 and 43 have only a short active length and form in the hose 29 a strip in which the inner faces of the hose in the region of the connecting parts 23 and 24 attain a certain adherence. The pressure applied by the rollers 42 and 43 is adjustable, so that a force with which the foil layers abut against one another in the region of the passages 23 and 24 can be adjusted.

Figure 9:
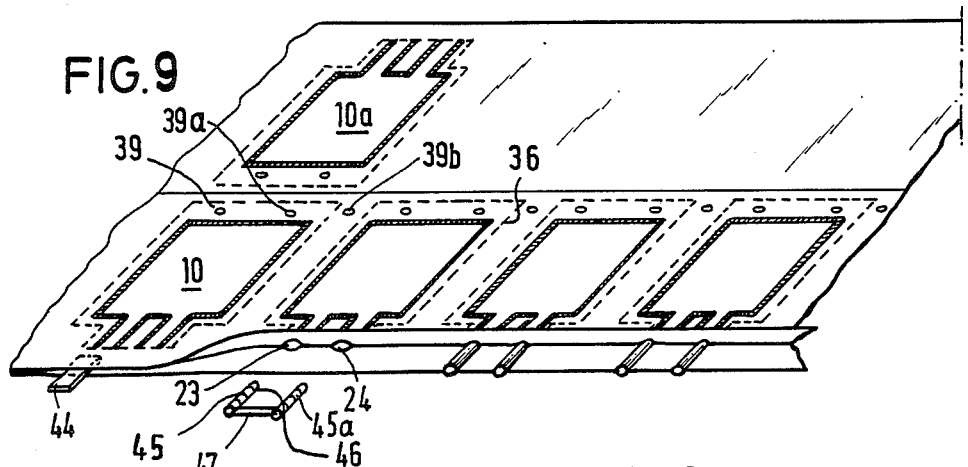
FIG. 9 is a perspective view showing connecting parts of the bag with plugs.

FIG. 9 shows simultaneous manufacture of two mirror-symmetrical, oppositely located bags 10 and 10a from a wide hose. FIG. 9 also shows the openings 39 and 39a at equal distances from one another, and shows additional openings 39b which are formed in the hose and arranged outside the bag limited by the perforations 36.

The hose edge 35 is cut in FIG. 9 by a cutter 44. Thereby the inlet openings of the passages 23 and 24 are released. This means that the passages 23 and 24 do not depend on the fact that their walls abut with a certain adherence against one another and thereby are tight. When first at a desired time point the hose edges are cut, the passages become accessible from outside. As can be seen from FIG. 9, the passages are provided with plugs 45 and 45a which have ring-shaped projections 45 to increase their adherence and to form barbs, so as to prevent unintentional withdrawal of the plugs from the openings. The plugs 45 and 45a are provided with a connecting rope 47 formed of injection-molded synthetic plastic material during their manufacture. Since the openings 23 and 24 of the bag are arranged in series and have equal distances or at least distances which at least are equal from one bag to the other, it is very simple to introduce the plugs 45 and 45a or similar elements by a machine into the passages 23 and 24.

Figure 10:
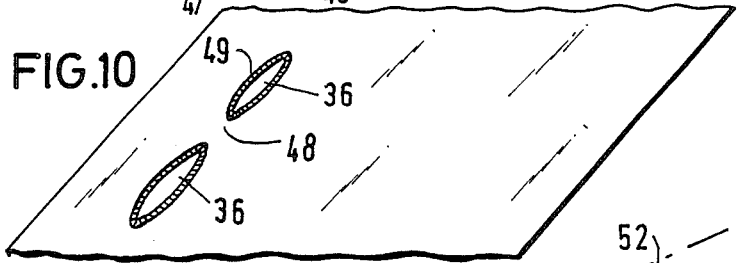
FIG. 10 is a view showing a partial section of a foil hose in the region of perforation cuts.

FIG. 10 shows more clearly the perforation cuts 36 provided so that a connecting web 48 is formed therebetween. The perforation cuts 36 are produced by a heated cutter with corrugations, so that the cut edges are connected with one another by welding seams 49. As a result of this, no "opening" of the hose takes place. Instead, the hose region between the bags remains hermetically closed.

Figure 11:
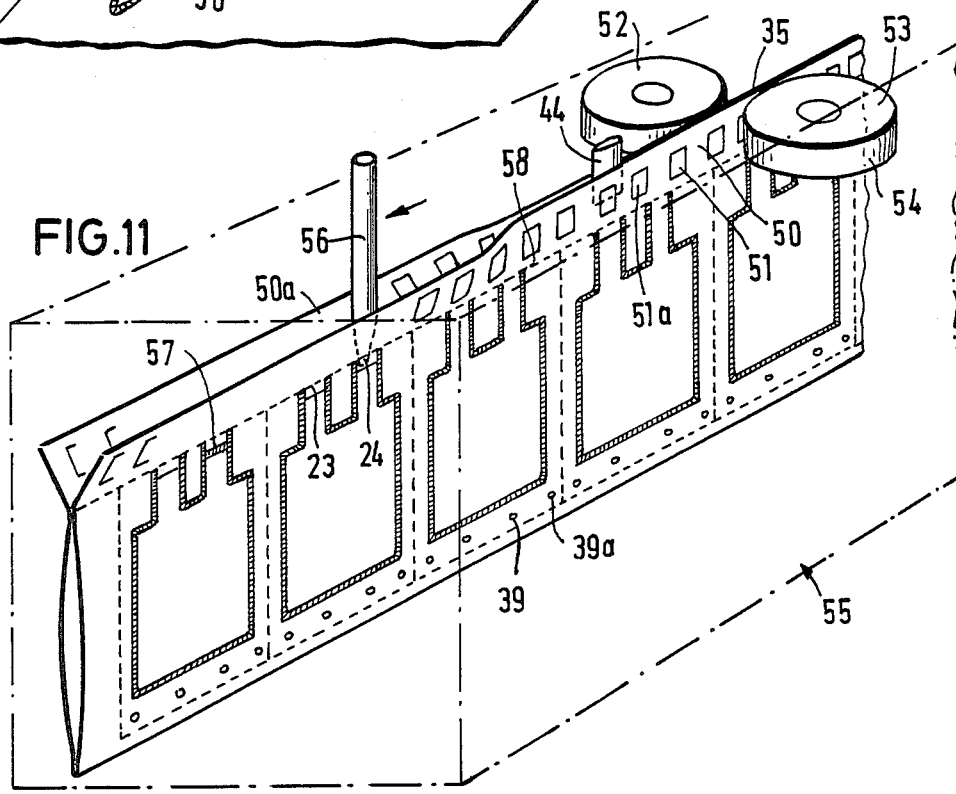
FIG. 11 is a perspective and substantially schematic view of the transportation and filling of a chain of bags.

FIG. 11 shows that edge regions 50 and 50a between the longitudinal edge 35 and the front end of the connecting parts or passages 23 and 24 have various functions. This end region is provided with window-like openings 51 and 51a which are advantageously rectangular, similarly to perforations in films for photographic purposes. These openings 51 and 51a are advantageously welded along their cutting lines by utilization of a heated punching tool, so that again no "opening" of the hose takes place. These openings serve for transportation and also for control of the filling device.

The above mentioned openings 51, or the like, are not absolutely necessary It is also possible to transport the chain of bags by transporting elements formed, for example, by opposite wheels 52 and 53 which have rough surfaces at their sides 54 facing toward the hose. Thereby the hose can be reliably transported. These rough surfaces are acceptable since the edge portions 50 which are slightly damaged by the rough surfaces are later separated after filling of the bag.

Reference numeral 55 identifies a filling station which is schematically shown by broken lines. The filling station is closed from outside and operates in aseptic conditions. Inside the filling station 55, the hose is cut at its longitudinal edge 35 by the cutter 44 so as to release inside the filling station the openings 23 and 24.

Filling pipes 56 with pointed front ends are introduced into the respective filling openings 24 and serve for supplying the solution into the bags. This introduction is simplified by the V-shaped walls of the edge portions 50 and 50a. During introduction of the filling pipes 56, the walls of the passage 24, which tightly abut against one another, are withdrawn from one another, so that the interior of the bag is accessible inside the filling chamber which operates under aseptic conditions.

After filling of the bag, the plugs 45 and 45a shown in FIG. 9 are inserted. After insertion of the plugs into the respective openings 23 and 24, in addition to the projections 46 they can be secured by a welding seam surrounding the same. It is also possible to provide the filled bag at its one piece connecting part with a closing welding seam 57, as shown in FIG. 11.

As soon as the bag is filled with liquid, it is converted from the flat shape to a three-dimensional spatial shape. The webs 44 shown in FIG. 10 are separated, so that the bag can be released from the hose. It is also possible to separate the bags from the hose at a later time. In any case, it is advantageous to separate the upper edge region 50 along the perforation line 58.

When in accordance with the inventive solution the inlet openings are first released in the filling chamber, there is a guarantee that the interior of the bag which has been produced sterile also remains sterile during filling. Thereby the bag can be reliably supported to its filling and transported further.

Despite the fact that the bag is manufactured sterile and is also filled in sterile condition, it is advantageous after filling or during filling in the filling chamber 45 to provide a sterilization with a temperature of approximately 120° C. and with utilization of vacuum, or a sterilization with gamma radiation.

It will be understood that each of the elements described above, or two or more together, may also find a useful application in other types of constructions differing from the types described above.

While the invention has been illustrated and described as embodied in a bag for infusion solutions and a hose for its manufacture, it is not intended to be limited to the details shown, since various modifications and structural changes may be made without departing in any way from the spirit of the invention.

Without further analysis, the foregoing will so fully reveal the gist of the invention that others can, by applying current knowledge, readily adapt it for various applications that, from the standpoint of prior art, fairly constitute essential characteristics of the generic or specific aspects of this invention.

What is claimed as new and desired to be protected by Letters Patent is set forth in the appended claims.

1. A method of manufacturing bags for infusion solutions and the like, comprising the steps of producing an elongated hose element of a synthetic thermoplastic foil in aseptic condition; laminating said elongated hose element by another outer thermoplastic foil by fixedly connecting said another thermoplastic foil to said hose element so as to form an elongated hose having two walls each composed of at least two connected foil layers; forming in said hose a plurality of shaped bag elements each having a body part and at least one connecting part which are of different widths and shapes, by a welding seam extending within said hose always through said four layers of said two walls of said hose and over and entire shaped contour of said body part and said connecting part of each of said bag elements; thereafter cutting said hose outwardly around said shaped welding seam of each of said bag elements by a shaped cut around said body part and said connecting part of each said shaped bag elements with said walls in contact with one another, so as to form a plurality of shaped bags each having a body part and at least one connecting part which are of different widths and shapes; filling each of said bags by introducing a filling element through said opening of said connecting part with spreading apart said walls in the region of said connecting part; and closing said connecting part of each of said bags.

2. A method as defined in claim 1, wherein said foil layers of each of said walls includes an inner layer and an outer layer, said inner layer being composed of a polyethylene, and said outer layer being composed of polyamide.

3. A method as defined in claim 1, wherein said foil layers of each of said walls include an inner layer and an outer layer, said inner layer being composed of polypropylene, and said outer layer being composed of polyamide.

4. A method as defined in claim 1, wherein said foil layers of each of said walls include an inner layer and an outer layer, said outer layer being composed of polyamide, said inner layer being composed of a material selected from the group consisting of polyethylene and polypropylene, each of said walls further including an intermediate layer located between said inner layer and said outer layer and composed of an oriented polyester with X-coating.

5. A method as defined in claim 1, wherein said foil layers of each of said walls includes an inner and an outer layer, each of said walls further including a first additional layer applied on said outer layer and a second additional layer applied on said first additional layer, said layers of each of said walls being composed in direction from outside toward inside of polyamide, polyethylene, polyvinylidene chloride and polyethylene.

6. A method as defined in claim 1, wherein said filling step includes first spreading apart said side walls of said hose so as to form a wedge-like channel, and then introducing said filling element through said opening of said connecting part with simultaneously guiding said filling element in the thus-formed wedge-like channel.

7. A method as defined in claim 1, wherein said cutting step includes cutting by forming a plurality of perforations which are spaced from one another so as to form a connecting web therebetween and which have edges formed by a welding seam connecting said foil layers of said walls with one another.

8. A method as defined in claim 7, wherein said cutting step includes forming said perforations by a heated cutter with corrugations.

9. A method as defined in claim 8, wherein said closing step includes closing said connecting part of each of said bags in aseptic condition.

10. A method as defined in claim 1, and further comprising the step of applying a pressure on said walls in the region of said connecting part before said cutting so as to provide an adherence of said walls toward one another in the region of said connecting part to prevent contamination of the latter.

11. A method as defined in claim 1; and further comprising the step of maintaining said hose hermetically closed with said walls in contact with one another, prior to said forming in said hose a plurality of shaped bag elements.

12. A method s defined in claim 1; wherein said cutting step includes cutting said hose so as to form an opening in said connecting part of each of said bag elements.

13. A method as defined in claim 1, wherein said filling step includes filling of each of said bags in aseptic condition.

14. A method as defined in claim 1, wherein said producing step includes producing an elongated hose element by extrusion at an extrusion temperature of about 170+ C.; said forming step includes welding by said shaped welding seam of said hose element in said outer thermoplastic foil with said hose element hermetically closed.

15. A method as defined in claim 1, wherein said laminating step includes laminating said elongated hose element by said outer thermoplastic foil such that a width of said outer thermoplastic foil is smaller than that of said hose element.

* * * * *